United States Patent [19]

Legutke et al.

[11] 4,310,713
[45] Jan. 12, 1982

[54] PRODUCTION OF 1,2-DICHLOROETHANE

[75] Inventors: Günter Legutke, Brühl; Gerhard H. Rechmeier; Harald Scholz, both of Erfstadt; Kurt Schuchardt, Bühl; Ernst Höller, Bornheim-Rösberg; Günther Liesenfelder, Erfstadt, all of Fed. Rep. of Germany

[73] Assignee: Hoechst Aktiengesellschaft, Fed. Rep. of Germany

[21] Appl. No.: 898,711

[22] Filed: Apr. 24, 1978

[30] Foreign Application Priority Data

Apr. 28, 1977 [DE] Fed. Rep. of Germany ....... 2718878
Sep. 21, 1977 [DE] Fed. Rep. of Germany ....... 2742409

[51] Int. Cl.$^3$ .......................................... C07C 17/156
[52] U.S. Cl. ................................................. 570/243
[58] Field of Search ...................... 260/659 A, 662 A; 570/243

[56] References Cited

U.S. PATENT DOCUMENTS

| | | | |
|---|---|---|---|
| 2,602,021 | 7/1952 | Belchetz | 260/659 A |
| 2,846,484 | 8/1958 | Fox | 260/659 A |
| 2,952,714 | 9/1960 | Milam et al. | 260/659 A |
| 3,488,398 | 1/1970 | Harpring et al. | 260/659 A |
| 4,071,572 | 1/1978 | Amato et al. | 260/659 A |

*Primary Examiner*—Delbert E. Gantz
*Assistant Examiner*—Joseph A. Boska
*Attorney, Agent, or Firm*—Connolly and Hutz

[57] ABSTRACT

1,2-dichloroethane is made by subjecting ethylene to an oxychlorination reaction with hydrogen chloride and a gas containing molecular oxygen in gas phase, at elevated temperature and in contact with a fluidized bed copper-II-chloride catalyst on a carrier, wherein the reaction gases are cooled under pressure in two condensation stages, condensed 1,2-dichloroethane and water are removed and the bulk of unreacted starting gas and inert gas are recycled. More specifically the reaction gases are delivered to a third condensation stage and cooled therein under pressure down to a temperature within the range 5° to 18° C. and to the extent necessary for the recycle gas to contain 0.5 to 3 volume % of 1,2-dichloroethane. Next, the recycle gas is directly admixed upstream of the reactor, with a quantity of pure oxygen necessary to replace consumed oxygen and re-establish an oxygen content of 12 to 25 volume % therein.

5 Claims, 1 Drawing Figure

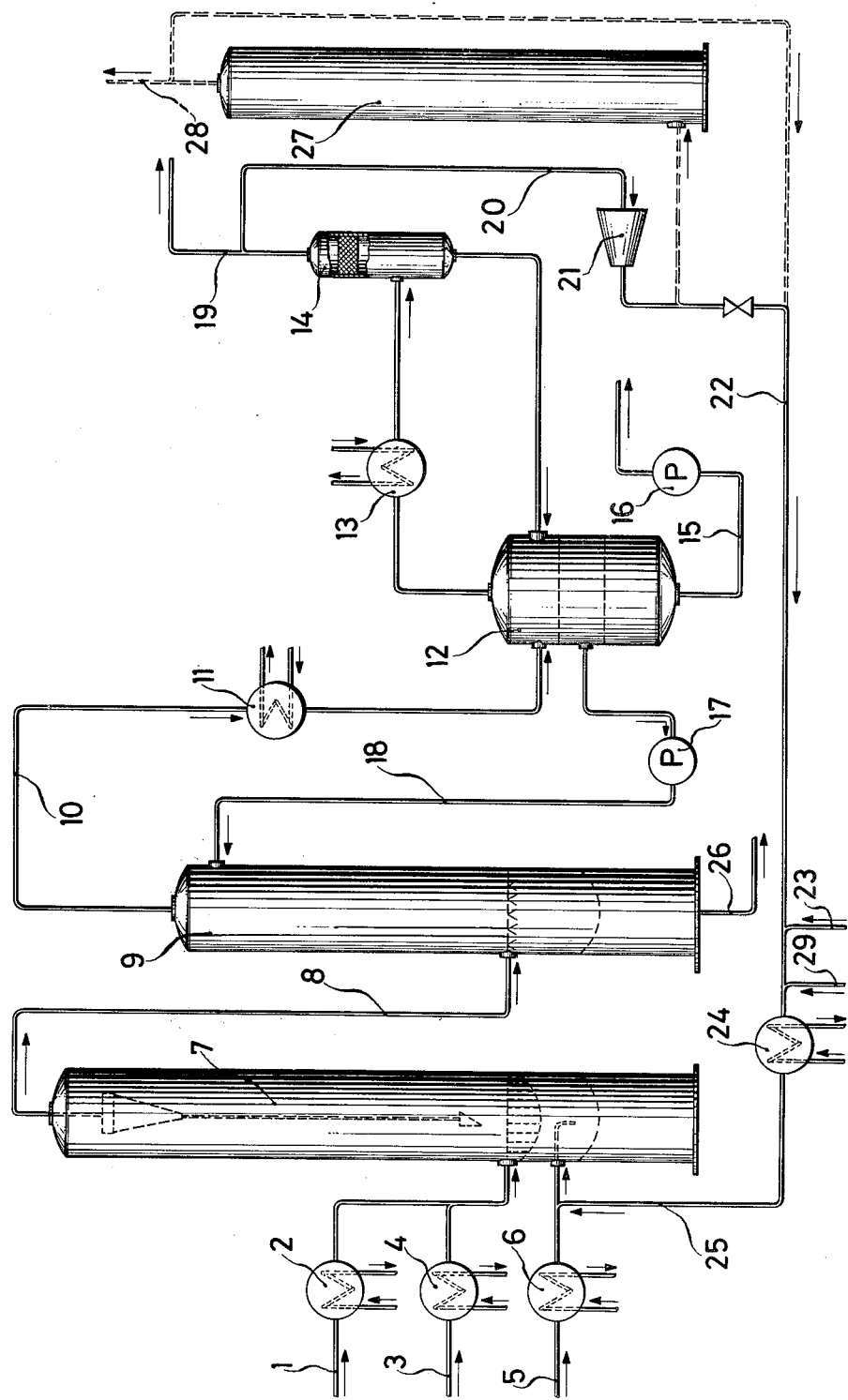

PRODUCTION OF 1,2-DICHLOROETHANE

This invention relates to a process for making 1,2-dichloroethane by subjecting ethylene to an oxychlorination reaction with hydrogen chloride and a gas containing molecular oxygen, preferably air, in gas phase at elevated temperature and in contact with a fluidized bed catalyst of copper-II-chloride on a carrier, wherein the reaction gases are cooled under pressure in two condensing stages, condensed 1,2-dichloroethane and water are removed, and the bulk of unreacted starting gas and inert gas are recycled.

This known oxychlorination reaction occurs in accordance with the following equation:

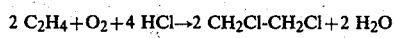

$$2\ C_2H_4 + O_2 + 4\ HCl \rightarrow 2\ CH_2Cl\text{-}CH_2Cl + 2\ H_2O$$

German Patent Specification "Auslegeschrift" 1,618,701 describes a process, wherein 1.6 to 2.5 mols of ethylene is reacted with 2.0 mols of hydrogen chloride and 0.6 to 1.0 mol of oxygen in the presence of 0.5 to 3.0 mols of carbon monoxide in contact with a copper-aluminum oxide catalyst, in contact with which the carbon monoxide is partially oxidized simultaneously to carbon dioxide. After condensation of the reaction products, it is necessary to recycle the unreacted starting materials, for reasons of economy. In order to enable the fluidized bed to be maintained, it is necessary to have a constant level of CO in the recycle gas. To this end, CO is oxidized to $CO_2$ above the catalyst made by a special process, and the resulting $CO_2$ is removed from the recycle gas by scrubbing the latter with a sodium hydroxide solution.

This process is not fully satisfactory in respect of the following points: (a) during the introduction of pure oxygen, special measures have to be taken as a precaution against spontaneous decomposition which may be caused by too high a content of ethylene and carbon monoxide and (b) it is necessary to scrub the recycle gas so as to free it from the carbon dioxide formed by oxidation. Next, it is necessary to recover separately dichloroethane and further chlorinated hydrocarbons from the scrubbing water.

Further processes have been described in German Patent Specifications "Auslegeschriften" 1,518,930; 1,518,931 and 1,518,932, wherein ethylene, oxygen and hydrogen chloride which are used in a molar ratio of (1.02 to 1.2) to (0.5 to 1.0) to 2.0, are reacted at 200° to 250° C. under a pressure of 0.7 to 3.5 bars in contact with a fluidized bed catalyst of $CuCl_2$ and $Al_2O_3$. In a first condensation stage, the reaction gases are cooled down to 70° to 100° C. and, in a second condensation stage, to 0° to 40° C. Incondensable gas portions are freed from residual 1,2-dichloroethane by scrubbing with an organic solvent and dichloroethane is ultimately recovered in a desorption column. The scrubbed gases which continue to contain fractions of chlorinated hydrocarbons and the organic solvent are either incinerated or allowed to escape into the atmosphere.

Coupled with the preferential use, in the process just described, of air as the oxygen carrier is the formation of important quantities of issuing gas containing only minor proportions of combustible compounds so that an additional fuel, e.g. fuel oil, has to be used in order to maintain the issuing gas at the temperature necessary for combustion.

Under the air pollution legislation of to-day, it is substantially not permissible for issuing gas containing chlorinated and other hydrocarbons, e.g. solvents, to be directly delivered to the atmosphere. The invariable loss of ethylene, dichloroethane and organic solvents which is associated therewith is a further adverse effect to consider and which adds to the difficulties encountered in the handling of important quantities of issuing gas.

A further cyclic process for making 1,2-dichloroethane by subjecting ethylene to an oxychlorination reaction has been described in German Patent Specification "Offenlegungsschrift" 2,626,133, wherein 80 to 98 volume % of incondensable unscrubbed gas is recycled. The recycle gas contains about 0.1 to 10 volume % each of ethylene and oxygen and less than 20 volume % of 1,2-dichloroethane, 2 to 20 volume % of recycle gas being removed during each cycle. The reaction gases are successively cooled first down to 81°–121° C. in a cooling tower, then down to 32° to 49° C. in a first condenser, and ultimately down to 27° to 38° C. in a second condenser. Substantially pure oxygen is used as the oxidizing gas in the process just described.

In the process described in German Patent Specification "Offenlegungsschrift" 2,626,133, the oxygen and starting reactants are jointly introduced into the reaction zone, which is hazardous as substantially pure oxygen is liable to come into contact with ethylene. Incidentally, the composition disclosed for the recycle gas in the Example of that specification does not permit substantially pure oxygen to be added to the gas upstream of the reactor, as the gas would be liable to undergo ignition.

The process of the present invention comprises more especially: delivering the reaction gases to a third condensation stage, cooling the reaction gases therein under pressure down to a temperature within the range 5° to 18° C. and to the extent necessary for the recycle gas to contain 0.5 to 3 volume %, preferably 0.5 to 1.5 volume %, of 1,2-dichloroethane, and directly admixing, upstream of the reactor, the recycle gas with a quantity of pure oxygen necessary to replace consumed oxygen and re-establish an oxygen content of 12 to 25 volume %, preferably 15 to 21 volume %, therein.

Further preferred features of the present process provide:
(a) for the recycle gas to be treated so as to establish an overall content of combustible ethylene, 1,2-dichloroethane, carbon monoxide and organic by-products of less than 3 to 6 volume % (which is the lower limit of explosion for an oxygen content of 25 to 12 volume %), the said overall content being established:
  (1) By using the ethylene, oxygen and hydrogen chloride starting reactants in a molar ratio of (1.00 to 1.10): (0.50 to 0.70): 2.00
  (2) by oxidizing 50 to 100, preferably 60 to 90 mol % of the carbon monoxide to carbon dioxide in contact with the catalyst, and
  (3) by maintaining the necessary content of inert gas of the recycle gas by supplying it with the calculated quantity of air and/or inert gas;
(b) for the recycle gas to be first freed partially or completely from combustible ethylene, 1,2-dichloroethane, carbon monoxide and organic by-products, which are removed therefrom jointly or separately by means of a customary absorbent, and to be then admixed with pure oxygen;

(c) for the quantity of recycle gas to be maintained constant and for the catalyst bed to be fluidized uniformly by means of the said constant quantity of recycle gas;

(d) for the catalyst performance to be controlled by varying the content of oxygen in the recycle gas, upstream of the reactor, within the range 12 to 25 volume %;

(e) for the composition of the recycle gas admixed with oxygen to be continually monitored analytically; and (f) for the reaction gases to be cooled under pressure in the first condensation stage down to 70° to 100° C. and in the second condensation stage down to 37° to 40° C.

The invention finally relates to a process for making 1,2-dichloroethane by subjecting ethylene to an oxychlorination reaction with hydrogen chloride and a gas containing molecular oxygen, preferably air, in gas phase at temperatures of 200° to 250° C., in contact with a copper-II-chloride fluidized bed catalyst on a carrier, wherein the reaction gases are cooled under pressure in a first condensation stage down to 70° to 100° C. and in a second condensation stage down to 0° to 40° C., condensed 1,2-dichloroethane and water are removed, and the bulk of unreacted starting gas and inert gas are recycled, which process comprises: cooling the reaction gases in the second condensation stage down to 37° to 40° C. and cooling them under pressure in a third condensation stage down to 5° to 18° C. to the extent necessary for the recycle gas to contain 0.5 to 3 volume %, preferably 0.5 to 1.5 volume %, of 1,2-dichloroethane, and directly admixing, upstream of the reactor, the recycle gas with a quantity of pure oxygen necessary to replace consumed oxygen and to re-establish an oxygen content of 12 to 25 volume %, preferably 15 to 21 volume %, therein.

The ethylene, oxygen and hydrogen chloride starting gases should preferably be employed in a molar ratio of (1.00 to 1.04): (0.50 to 0.60): 2.00. It is also good practice to effect the reaction under a pressure of 0.7 to 3.5 bars and to maintain the three condensation stages under the same pressure. A catalyst suitable for use in the present process is, e.g. the $CuCl_2/Al_2O_3$-catalyst disclosed in German Patent Specification 1,518,932. The recycle gas is directly recycled to the reactor, i.e. it is left unscrubbed with sodium hydroxide solution.

The 1,2-dichloroethane which is retained in the recycle gas enables the ethylene conversion rate in the reactor to be increased without increased combustion of ethylene to CO and $CO_2$. This means in other words that an additional quantity of ethylene undergoes conversion to 1,2-dichloroethane. On the other hand, 1,2-dichloroethane together with ethylene, carbon monoxide and organic by-products adversely affects the lower limit of explosion inasmuch as these substances are not permitted to exceed a maximum of 3 to 6 volume %, depending on the oxygen content in the recycle gas.

The $CuCl_2/Al_2O_3$-catalyst used in the process of this invention enables 50 to 100 mol %, more specifically 60 to 90 mol %, of the CO to be oxidized to $CO_2$, under the conditions described, so that the recycle gas is soon found to present a constant CO-content of 0.5 to 2.5 volume %. In clear contrast with the process described in German Patent Specification "Auslegeschrift" 1,618,701, it is possible in the present process to recycle carbon dioxide substantially in the absence of adverse effects on catalyst performance.

Various proposals have already been made relative to the work up of the incondensable gas. Thus, for example, it has been proposed to subject the gas to catalytic combustion and to recover hydrogen chloride, or to further treat it with chlorine so as to obtain 1,2-dichloroethane, or to pass the entire quantity of gas through an absorption facility and free it from residual proportions of hydrocarbons, or to scrub it with an organic solvent and then incinerate it. These procedures are however very expensive.

In the present process, it is merely necessary, in order for the quantity of recycle gas to be kept constant, to remove the quantities of CO and $CO_2$ which are invariably obtained by the combustion of ethylene during each passage through the fluidized bed reactor. The quantity which is to be removed corresponds substantially to 1 to 10 volume % of the quantity of recycle gas. In order to avoid the minor loss of desirable material which is associated with the removal of such small quantity of off-gas, it is possible to contact the off-gas with an absorbent, e.g. active carbon, and add the water/hydrocarbon-mixture, which is obtained on regenerating the active carbon, to the condensate of the second condensation stage. Needless to say it is also possible to deliver the above small quantity of off-gas to an incineration facility.

A further advantage of the present process resides in the fact that the catalyst performance can be varied by means of the quantity of fresh oxygen which is supplied to replace consumed oxygen. It is more particularly possible to produce space/time-yields within the range 10 to 100% by appropriately varying the supply of fresh oxygen, the quantity of recycle gas necessary to maintain the catalyst bed fluidized being kept constant. This enables the reactor to be operated within the above wide range according to the requirements in each particular case.

The present process permits 1,2-dichloroethane to be produced in improved yields. Based on the ethylene used the yields are increased by the proportion of ethylene which in the processes described heretofore undergoes combustion together with the off-gas. More specifically, the yield is improved by 2.5 to 5.0% of the theoretical. The yield, based on hydrogen chloride, is 98 to 100% of the theoretical.

The process of the present invention will now be described with reference to the accompanying drawing.

Ethylene, coming from a conduit 1 and a preheater 2, and hydrogen chloride, coming from a conduit 3 and a preheater 4, are jointly introduced into a fluidized bed reactor 7, which is also fed with air coming from a conduit 5 and a preheater 6. Placed in the reactor 7 is a copper-II-chloride catalyst. The oxychlorination is exothermal. By means of a hot water circulation system, the temperature is maintained e.g. at 220° to 235° C. The pressure prevailing in the whole system is maintained at 3 bars. Via a cyclone, the gas is admitted through a conduit 8 to a first condensation stage 9, wherein it is cooled down to about 80° C. by means of reaction water which comes from a container 12 and is pumped by means of a pump 17 through a conduit 18. Unconsumed hydrogen chloride and the bulk of reaction water are condensed. Via a conduit 10 and a cooler 11 (second condensation stage), the gas is cooled down to about 40° C. 1,2-dichloroethane and residual water are condensed and coarsely separated from one another in a separator 12. The water is recycled to the first condensation stage 9, removed through a conduit 26 and worked up. Crude dichloroethane is taken from the separator 12 through a conduit 15 and a pump 16, and delivered to a purification stage. Incondensed gas is cooled in a cooler 13 (third condensation stage) down to 5° to 18° C. to the extent necessary to retain 0.5 to 3 volume % of 1,2-dichloroethane therein. Post-condensed 1,2-dichloroethane is collected in a separator 14 and recycled to the separator 12. The remaining gas is recycled to the reactor 7 via a conduit 20, compressor 21, conduit 22, preheater 24 and conduit 25. Prior to recycling the gas, it is thoroughly admixed in conduit 22 with the quantity of oxygen (coming from conduit 23) necessary to have a desirable total $O_2$-content of 12 to 25 volume %. It is also possible to provide, downstream of the compressor 21, an absorption facility 27 containing a liquid or solid absorbent, through which all incondensed gas should conveniently be passed, prior to its being admixed with oxygen in conduit 22. The composition of the gas admixed with oxygen upstream of the reactor is continually monitored analytically in order to avoid the formation of ignitable mixtures in the recycle gas. As soon as the necessary quantity of gas is available, the supply of air through the conduit 5 is throttled, e.g. the gas is admixed with the quantity of air necessary to maintain its content of nitrogen approximately constant. The quantity of gas is maintained constant by the removal, through conduit 19 or 28, of a quantity which substantially corresponds to the proportion of ethylene which undergoes combustion to CO and $CO_2$. The quantity of gas so removed is worked up in known manner. Conduit 29 is used for the introduction of inert gas.

In the following Examples 1 through 6, use was made of a fluidized bed reactor 3.0 meters wide and altogether 29.9 meters high. The catalyst was a copper-II-chloride catalyst which contained about 4 weight % of copper and was deposited on aluminum oxide. The catalyst was used in an average quantity of 48.700 kilograms.

EXAMPLE 1

(Prior art process; single gas passage with the use of air as the oxygen carrier)

Ethylene and hydrogen chloride which were used in a molar ratio of 1.05 to 2.00, were heated separately to 145° to 150° C. and admitted jointly to the distributing tray of the reactor. At the same time, air was preheated to 150° to 160° C. and introduced into the reactor, downstream of the tray. The molar ratio of ethylene, hydrogen chloride and oxygen inside the tray was 1.05:2.00:0.63. The compounds substantially underwent conversion to 1,2-dichloroethane while heat was set free. The heat set free was abstracted in known manner by cooling with water maintained under high pressure, and used for the generation of steam. The reactor was maintained at a temperature of 223° C. and under a pressure of 3 bars. 1,2-dichloroethane was separated by condensing it in two stages (first stage: 90° C., second stage: 10° C.). Incondensable gas was absorbed by scrubbing it with an aromatic hydrocarbon absorbent and delivered to an incineration facility. Downstream of the scrubbing stage, the gas contained:

| | | |
|---|---|---|
| oxygen | 9 volume % | |
| nitrogen | 87.75 volume % | |
| carbon monoxide | 0.5 volume % | |
| carbon dioxide | 1.5 volume % | |
| 1,2-dichloroethane | 50 to 100 ppm | |
| ethylene | 1.2 volume % | |
| aromatic hydrocarbons | 20 ppm | |

The low calorific value made it necessary for the gas to be brought to combustion temperature with the aid of a foreign fuel, e.g. fuel oil.

The aromatic absorbent was freed from dissolved hydrocarbons in a separate desorption facility. The absorbent was used again in the scrubbing stage while the desorbed hydrocarbons were recycled to the second condensation stage.

The ethylene conversion rate was 95.9% and the catalyst performance was 255 g of 1,2-dichloroethane per kg of catalyst per hour. 1,2-dichloroethane was obtained in a yield of 92.1% of the theoretical, based on the ethylene used.

The following Examples 2 to 6 describe the process of this invention.

EXAMPLE 2

Ethylene, hydrogen chloride and air, which were used in a molar ratio of 1.04 to 2.00 to 0.55 $O_2$ (in the form of air) were introduced into the reactor in the manner described in Example 1. The reactor was filled once. Next, the supply of air was stopped and incondensable reaction gas (which was not delivered to a scrubbing station for absorption) was compressed to 5.5 bar, and treated with pure oxygen so as to establish an oxygen content of 21 volume %. Next, it was preheated to 150° to 160° C. and introduced into the reactor downstream of the distributing tray therein. The reaction heat was dissipated and the condensation was effected as described in Example 1, save that the reaction gas was cooled in the second condensation stage down to 37° to 40° C. and in the third condensation stage down to 7° C.

Prior to its being admixed with oxygen, the recycle gas contained:

| | | |
|---|---|---|
| oxygen | 10.3 | volume % |
| nitrogen | 32.70 | volume % |
| carbon monoxide | 2.5 | volume % |
| carbon dioxide | 52.5 | volume % |
| 1,2-dichloroethane | 0.81 | volume % |
| ethylene | 0.62 | volume % |
| further combustible ingredients | <0.5 | volume % |

The ethylene conversion rate was 99.81% as only minor proportions of the gas had to be removed. Only those quantities of gas, which were obtained by the combustion of ethylene to carbon monoxide and carbon dioxide, were removed. 1,2-dichloroethane was obtained in a yield of 96.48% of the theoretical based on the ethylene used. The catalyst performance was 280 g per kg of catalyst per hour.

EXAMPLE 3

Ethylene, hydrogen chloride and air were introduced into the reactor as described in Example 2. The recycle gas was admixed with the quantity of oxygen necessary to establish an oxygen content of 16.5 volume %.

The catalyst performance was 166 g of 1,2-dichloroethane per kg of catalyst per hour.

The ethylene conversion rate was 99.78% and 1,2-dichloroethane was obtained in a yield of 96.52% of the theoretical, based on the ethylene used.

Prior to its being admixed with oxygen, the recycle gas contained:

| | |
|---|---|
| oxygen | 10.5 volume % |
| nitrogen | 55.4 volume % |
| carbon monoxide | 2.2 volume % |
| carbon dioxide | 30.0 volume % |
| 1,2-dichloroethane | 0.3 volume % |
| ethylene | 0.6 volume % |
| further combustible ingredients | <0.5 volume % |

EXAMPLE 4

The conditions were the same as those used in Examples 2 and 3 save that an oxygen content of only 13.0 volume % was established in the recycle gas. The same quantities of catalyst and recycle gas were used, but the catalyst performance was found to drop to 84 g of 1,2-dichloroethane per kg of catalyst per hour.

The conversion rate and yield remained substantially unchanged. The ethylene conversion rate was 99.71% and 1,2-dichloroethane was obtained in a yield of 96.49% of the theoretical, based on the ethylene used. Prior to its being admixed with oxygen, the recycle gas contained:

| | | |
|---|---|---|
| oxygen | 11 | volume % |
| nitrogen | 70.10 | volume % |
| carbon monoxide | 1.72 | volume % |
| carbon dioxide | 15.3 | volume % |
| 1,2-dichloroethane | 0.79 | volume % |
| ethylene | 0.6 | volume % |
| further combustible ingredients | <0.5 | volume % |

EXAMPLE 5

The procedure was the same as that described in Example 2, i.e. an oxygen content of 21 volume % was established in the recycle gas. In the third condensation stage, the reaction gas was cooled down to 14° C. under a pressure of 3 bars. Prior to its being admixed with oxygen, the recycle gas contained:

| | | |
|---|---|---|
| oxygen | 10.3 | volume % |
| nitrogen | 32.5 | volume % |
| carbon monoxide | 2.40 | volume % |
| carbon dioxide | 52.00 | volume % |
| 1,2-dichloroethane | 1.20 | volume % |
| ethylene | 0.38 | volume % |
| further combustible ingredients | <0.5 | volume % |

The ethylene conversion rate was 99.86% and 1,2-dichloroethane was obtained in a yield of 96.62% of the theoretical, based on the ethylene used. As shown in the Table hereinafter, the recycle gas was found to contain less ethylene although the combustion of ethylene could not be found to have increased.

The catalyst performance was 280 g of 1,2-dichloroethane per kg of catalyst per hour.

Gas which was removed through the conduit 19 was passed over an active carbon filter to recover 1,2-dichloroethane therefrom.

EXAMPLE 6

The procedure was the same as in Example 2. i.e. an oxygen content of 21 volume % was established in the recycle gas. Downstream of the condensation stage, the total quantity of gas was passed through an absorption facility 27 containing aromatic hydrocarbons (alkyl benzenes) as absorbents so as to be freed from 1,2-dichloroethane and organic by-products. The bulk of the gas was then recycled as described hereinabove. Prior to its being admixed with oxygen, the recycle gas contained:

| | | |
|---|---|---|
| oxygen | 10.6 | volume % |
| nitrogen | 32.8 | volume % |
| carbon monoxide | 2.5 | volume % |
| carbon dioxide | 52.5 | volume % |
| ethylene | 0.63 | volume % |

Residual gas was taken from the conduit 28 and directly delivered to an incineration facility. The gaseous hydrocarbons which were absorbed in the absorption facility were desorbed and introduced into the separator 12.

The catalyst performance was 280 g of 1,2-dichloroethane per kg of catalyst per hour, and 1,2-dichloroethane was obtained in a yield of 96.49% of the theoretical. The ethylene conversion rate was 99.82%.

| Ex. No. | 1,2-dichloroethane yield, based on ethylene used % of theoretical | Ethylene conversion rate % | Catalyst performance (g 1,2-dichloroethane per kg catalyst per hour) | $C_2H_4$-combustion to CO and $CO_2$ weight % | 1,2-dichloroethane prior to oxygen addition through conduit 23 volume % | CO conversion to $CO_2$ mol % | Sum of combustible hydrocarbons and carbon monoxide prior to oxygen addition through conduit 23 volume % |
|---|---|---|---|---|---|---|---|
| 1 | 92.1 | 95.9 | 255 | 3.3 | 0.9 | — | 1.712 |
| 2 | 96.48 | 99.81 | 280 | 3.3 | 0.81 | 70 | 4.43 |
| 3 | 96.52 | 99.78 | 166 | 3.26 | 0.80 | 60 | 4.1 |
| 4 | 96.49 | 99.71 | 84 | 3.27 | 0.79 | 55 | 3.61 |
| 5 | 96.62 | 99.86 | 280 | 3.24 | 1.20 | 72 | 4.48 |
| 6 | 96.49 | 99.82 | 280 | 3.28 | 0 | 70 | 3.13 |

We claim:

1. In a process for making 1,2-dichloroethane by subjecting ethylene to an oxychlorination reaction with hydrogen chloride and a gas containing molecular oxygen in gas phase, at temperatures of 200° to 250° C., in contact with a fluidized bed catalyst consisting substantially of copper-II-chloride on a carrier, wherein the reaction gases are cooled under pressure in a first condensation stage down to 70° to 100° C. and in a second condensation stage down to 0° to 40° C., condensed 1,2-dichloroethane and water are removed, and the bulk of unreacted starting gas and inert gas are recycled, the improvement which comprises cooling the reaction gases in the second condensation stage down to 37° to 40° C. and cooling them under pressure in a third condensation stage down to 5° to 18° C. to the extent necessary for the recycle gas to contain 0.5 to 3 volume % of 1,2-dichloroethane; directly admixing, upstream of the reactor, the recycle gas with a quantity of pure oxygen necessary to replace consumed oxygen and to re-establish an oxygen content of 12 to 25 volume % therein; and establishing an overall content of the combustible components ethylene, 1,2-dichloroethane, carbon monoxide and organic by-products which is below the lower limit of explosion of 3 to 6 volume % for an oxygen content of 25 to 12 volume %, the said overall content being established (a) by using the ethylene, oxygen and hydrogen chloride starting reactants in a molar ratio of (1.00 to 1.10): (0.50 to 0.70): 2.00,
(b) by oxidizing 50 to 100 mol % of the carbon monoxide to carbon dioxide in contact with the catalyst, and
(c) by maintaining the necessary content of inert gas of the recycle gas by supplying it with the calculated quantity of a substance selected from air and inert gas.

2. In a process for making 1,2-dichloroethane by subjecting ethylene to an oxychlorination reaction with hydrogen chloride and a gas containing molecular oxygen in gas phase, at temperatures of 200° to 250° C., in contact with a fluidized bed catalyst consisting substantially of copper-II-chloride on a carrier, wherein the reaction gases are cooled under pressure in a first condensation stage down to 70° to 100° C. and in a second condensation stage down to 0° to 40° C., condensed 1,2-dichloroethane and water are removed, and the bulk of unreacted starting gas and inert gas are recycled, the improvement which comprises cooling the reaction gases in the second condensation stage down to 37° to 40° C. and cooling them under pressure in a third condensation stage down to 5° to 18° C. to the extent necessary for the recycle gas to contain 0.5 to 3 volume % of 1,2-dichloroethane; freeing the recycle gas at least partially from combustible ethylene, 1,2-dichloroethane, carbon monoxide and organic byproducts, which are removed therefrom jointly or separately by means of a customary absorbent; admixing, upstream of the reactor the recycle gas with a quantity of pure oxygen necessary to replace consumed oxygen and to re-establish an oxygen content of 12 to 25 volume % therein; and establishing an overall content of the combustible components ethylene, 1,2-dichloroethane, carbon monoxide and organic by-products which is below the lower limit of explosion of 3 to 6 volume % for an oxygen content of 25 to 12 volume %, the said overall content being established (a) by using the ethylene, oxygen and hydrogen chloride starting reactants in a molar ratio of (1.00 to 1.10): (0.50 to 0.70): 2.00,
(b) by oxidizing 50 to 100 mol% of the carbon monoxide to carbon dioxide in contact with the catalyst, and
(c) by maintaining the necessary content of inert gas of the recycle gas by supplying it with the calculated quantity of a substance selected from air and inert gas.

3. A process as claimed in any one of claims 1 or 2, wherein the quantity of recycle gas is maintained constant and the catalyst bed is fluidized uniformly by means of the said constant quantity of recycle gas.

4. A process as claimed in any one of claims 1 or 2, wherein the catalyst performance is controlled by varying the content of oxygen in the recycle gas, upstream of the reactor, within the range 12 to 25 volume %.

5. A process as claimed in any one of claims 1 or 2, wherein the composition of the recycle gas admixed with oxygen is continually monitored analytically.

* * * * *